(12) United States Patent
Guarna et al.

(10) Patent No.: US 6,514,912 B1
(45) Date of Patent: Feb. 4, 2003

(54) USE OF BENZO[C]QUINOLIZINE DERIVATIVES AS PLANT GROWTH REGULATORS

(75) Inventors: Antonio Guarna, Seano Carmignagno (IT); Mario Serio, Bagno a Ripoli (IT)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/480,238

(22) Filed: Jan. 10, 2000

Related U.S. Application Data

(63) Continuation of application No. PCT/EP98/04737, filed on Jul. 27, 1998.

(51) Int. Cl.[7] .................. A01N 43/42; C07D 455/04
(52) U.S. Cl. ................... 504/245; 546/95; 514/294
(58) Field of Search .................... 514/294; 546/95; 504/245

(56) References Cited

U.S. PATENT DOCUMENTS 6,303,622 B1 * 10/2001 Guarna ...................... 514/294

FOREIGN PATENT DOCUMENTS

WO          9729017          8/1997

OTHER PUBLICATIONS

Chemical Abstracts, vol. 126, No. 25; Jun. 23, 1997, No. 327248.
Chemical Abstracts, vol. 124, No. 23, Jun. 3,1996, No. 309107.
Derwent Publication Ldt, Database WPI Week 9519, Class C03.
Journal of the Chemical Society, No. 19, pp. 3291–3296, 1971.
Trends in Genet., vol. 9, No. 5, p:167, May 1993.
Proc. Nat. Acad. Sci. USA, vol. 93, pp. 12066–12071, Oct. 1996.

* cited by examiner

*Primary Examiner*—Evelyn Mei Huang
(74) *Attorney, Agent, or Firm*—Hedman & Costigan, P.C.

(57) ABSTRACT

Disclosed are compositions of benzo(c)quinolizine derivatives and methods for promoting plant and seed growth. The compounds are benzo[c]quinolizine derivatives which exert an inhibiting effect on the 5-alpha-reductase enzymes. The compounds selectively affect the growth of plants, improving morphogenesis and development of commercially useful plants while acting as herbicides to inhibit weed development.

12 Claims, No Drawings

USE OF BENZO[C]QUINOLIZINE DERIVATIVES AS PLANT GROWTH REGULATORS

The present application is a continuation of and claims priority to International Application No. PCT/EP98/04737, filed Jul. 27, 1998 and Italian Application Serial No. FL97A000193 filed Aug. 1, 1999.

SCOPE OF INVENTION

The present invention regards the use of benzo[c] quinolizine derivatives of general formula (I)

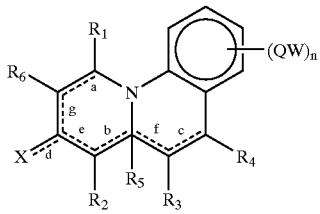

in which:

$R_1$, $R_2$, $R_3$, $R_4$ and $R_6$, which are the same or different from one another, are chosen from the group consisting of H, $C_{1-8}$ alkyl, $C_{2-8}$ alkenyl, $C_{2-8}$ alkynyl, $C_{3-6}$ cycloalkyl, aryl, heterocycle, halogen, CN, azide, NRR', $C_{1-8}$ alkylamine, arylamine, $C_{1-8}$ alkyloxy, aryloxy, COOR, and CONRR', where R and R', which are the same or different from one another, are chosen from the group consisting of H, $C_{1-8}$ alkyl, aryl, heterocycle, aryl-$C_{1-8}$ alkyl, and cyclo-alkyl; $R_5$ is chosen from the group consisting of H, $C_{1-8}$ alkyl, aryl-$C_{1-8}$ alkyl, COOR, CN, aryl, heterocycle, and the $C_{1-8}$ alkyl heterocycle;

X is chosen from the group consisting of O, C(=O)R, COOR, $NO_2$, and CONNR', in which R and R' are as defined above; Q is chosen from the group consisting of single-bond, $C_{1-8}$ alkyl, $C_{2-8}$ alkenyl, $C_{2-8}$ alkynyl, cyclo-alkyl, CO, CONR, and NR, where R is as defined previously;

W is chosen from the group consisting of H, $C_{1-8}$ alkyl, $C_{2-8}$ alkenyl, $C_{2-8}$ alkynyl, cycloalkyl, trifluoromethyl, $C_{1-8}$ alkoxy, $C_{1-8}$ alkoxy-$C_{1-8}$ alkyl, aryl-$C_{1-8}$ alkyl, aryl, aryloxy, arylamine, $C_{1-8}$ alkyl-carbonyl, arylcarbonyl, halogen, CN, NRR', $C_{1-8}$ alkylamine, and heterocycle, in which the alkyl, alkenyl, alkynyl, cycloalkyl, aryl, and heterocycle groups may be substituted:

n is 1, 2, 3, or 4;

the mark ------- indicates that the respective bonds a,b,c, d,e,f, and g are single or double bonds, considering that when b or f are a double bond, the $R_5$ group is absent.

The salts of the compounds of formula (I) are also included in the invention.

STATE OF THE ART

It is known that steroidal enzymes have a considerable importance both in the field of medicine and in that of sciences related to the development of agriculture and foodstuffs. However, whilst the physiological role of steroids in man has been amply studied and documented, the physiological role of steroids in the vegetable world is less well known.

The growth of plants is governed by complex interactions between environmental signals and internal factors. Light regulates many processes of development throughout the life cycles of the plant, starting from seed germination right up to flower development (J. Chory, Trends, Genet., 1993, 9, 167). In the presence of light, the growth of hypocotyledons is inhibited, cotyledons expand, leaves develop, chloroplasts differentiate producing chlorophyll, and a large number of light-inducible genes are activated.

It has been recently suggested that brassinosteroids, which are the most widespread steroids in higher plants, may be directly involved in the response of plants to light (Chory et al., Proc. Natl. Acad. Sci. 1996, 93, 12066). However, the interactions between phototransduction and hormones are not yet well known. Brassinolid is the steroid that has a fundamental role in the development of plants under the effect of light and has been identified in the larger part of higher plants. It is generated through a metabolic cascade in which campesterol (a compound similar to cholesterol) is reduced to campestanol. The enzyme which is responsible for this reduction is a 5-alpha-reductase steroidal enzyme, named DET2 after the gene of the same name isolated for the plant Arabidopsis, which presents a sequence analogy of up to 80% on the conservative amino acids of the isoenzymes 1 and 2 of the 5-alpha-reductase of humans and rats. The genetic mutations that inactivate DET2 do not allow production of brassinolid and determine deep alterations in the development of seeds and in Arabidopsis plants in the dark or under the effect of light.

In the dark, the plants mutated genetically in DET2 present short and thick hypocotyledons, accumulate anthocyanins, have open and expanded cotyledons, and develop primary-leaf buds. In the light, the mutated plants are smaller and of a darker green, have a reduced apical dominance and male fertility. In addition, they have different responses to light, with delayed flowering and delayed ageing of leaves and chlorophyll (J. Li et al., Science, 1996, 272, 398).

These alterations of the mutating species are reversed with the exogenous addition of brassinolid to the growth medium (J. Li et al., Proc. Natl. Acad. Sci., 1997, 94, 3554-3559).

DETAILED DESCRIPTION OF THE INVENTION

It has now been surprisingly found that the products of formula (I) as described above exert an inhibiting action on the 5-alpha-reductase steroidal enzymes, in particular on the DET2 enzyme, and hence are able to affect selectively the growth of plants in the dark and in the light, and can therefore be used as phytopharmaceutical substances in the field of agriculture and foodstuffs both as substances capable of improving the morphogenesis and development of plants that are commercially useful and as potential herbicides that inhibit the development of weeds.

In the products of formula (I) according to the present invention, by $C_{1-8}$, alkyl, $C_{1-8}$, alkenyl and $C_{1-8}$ alkynyl group are meant alkyl radicals, either linear or branched, such as methyl, ethyl, propyl, isopropyl, butyl, pentyl, hexyl, heptyl, octyl, ethylene, propene, butene, isobutene, acetylene, propyne, butyne, etc.

By the term cyclo-alkyl the following are meant: cyclopropane, cyclobutane, cyclopentane, cyclohexane, cycloheptane, cyclo-octane, norbornane, camphane, and adamantane.

By the term aryl the following are meant: phenyl and naphthyl.

By the term heterocycle the following are meant in particular: saturated or aromatic heterocycles containing one or more nitrogen atoms, and more in particular, pyridine, imidazole, pyrrole, indole, triazoles, pyrrolidine, and piperidine.

By halogen the following are meant: fluorine, chlorine, bromine, and iodine.

The substituents of the aforementioned W groups are preferably: halogen, OR, phenyl, NRR', CN, COOR, CONRR', and $C_{1-8}$ alkyl (in which R and R' are as defined above).

In particular, according to the present invention the products of formula (I) are preferred in which:
$R_5$=H, heterocycle, aryl-$C_{1-8}$, alkyl, or $C_{1-8}$ alkyl heterocycle;
X=0;
Q=single-bond, CO, CONR, or NR (where R is as defined above);
W=H, F, Cl, Br, Me, tert-butyl, $C_{1-8}$, alkoxy, 2,5-dimethylhexyl, trifluoromethyl, 2,5-(di-trifluoromethyl)-phenyl, 4-methoxy-phenyl, 4-fluoro-phenyl, phenyl, phenyl-$C_{1-8}$ alkyl, $C_{1-8}$ alkylcarbonyl, or phenylcarbonyl;
n=1 or 2;
$R_1, R_2, R_3, R_4, R_6$=H, Me, CN, phenyl, COOR, or CONRR' (where R and R' are as defined above).

Products preferred according to the present invention are:
1,2,4,4a,5,6 hexahydro-(11H)-benzo[c]quinolizin-3-one;
8-chloro-1,2,4,4a,5,6 hexahydro(11H)-benzo[c]quinolizin-3-one;
1,2,4,4a,5,6 hexahydro-8-methyl(11H)-benzo[c]quinolizin-3-one;
1,2,4,4a,5,6 hexahydro-4-methyl-(11H)-benzo[c]quinolizin-3-one;
1,2,4,4a,5,6 hexahydro-1-methyl-(11H)-benzo[c]quinolizin-3-one;
1,2,5,6-tetrahydro-(11H)-benzo[c]quinolizin-3- one;
8-chloro-1,2,5,6-tetrahydro-(11H)-benzo[c]quinolizin-3-one;
8-methyl-1,2,5,6-tetrahydro-( 11H)-benzo[c]quinolizin-3-one;
4-methyl-1,2,5,6-tetrahydro-( 11H)-benzo[c]quinolizin-3-one;
1-methyl-1,2,5,6-tetrahydro-( 11H)-benzo[c]quinolizin-3-one;
4 ,4a, 5,6-tetrahydro-(11H)-benzo[c]quinolizin-3-one;
4a-benzyl4,4a,5,6-tetrahydro-(11H)benzo[c]quinolizin-3-one;
8-chloro4a-benzyl -4,4a,5,6-tetrahydro-(11H)-benzo[c]quinolizin-3 -one;
5,6-dihydro-(11H)benzo[c]quinolizin-3-one;
8-chloro-4,4a,5,6-tetrahydro-(11H)-benzo[c]quinolizin-3-one;
8-chloro-1-methyl-4,4a,5,6-tetrahydro-(11 H)-benzo[c]quinolizin-3-one;
8-methyl4,4a,5,6-tetrahydro-(11 H)-benzo[c]quinolizin-3-one;
(cis) and (trans) 4-methyl4,4a,5,6-tetrahydro-( 11H)-benzo[c]quinolizin-3-one; 8-chloro4-methyl-1 ,2,5,6-tetrahydro-(11H)-benzo[c] quinolizin-3-one;
4,8-dimethyl-1,2,5,6-tetrahydro-(11H)-benzo[c]quinolizin-3-one;
(cis) and (trans) 4,8-dimethyl4,4a,5,6-tetrahydro-(11H)-benzo[c]quinolizin-3-one;
(cis) and (trans) 8-chloro4-methyl4,4a,5,6-tetrahydro-( 11H)-benzo[c]quinolizin-3- one.

The compounds according to the present invention can be prepared, for example, starting from compounds such as hydrocarbostyril which is commercially available or can be prepared according to known techniques. The amide group of this compound is protected via a protecting group, which may be, for example, tertbutoxycarbonyl (t-boc). This produces a compound which is then reduced using, for example, Grignard reagent. This compound is then reacted with silylether, produced "in situ" starting from vinyl ketones with a silylating agent such as trimethylsilyltrifluoromethansulphonic anhydride (TMSOTf) and thereafter hydrolyzed, for example, in sodium hydrogen carbonate, to give the compounds of formula (1) where X=0.

The possible introduction of the double bonds and the transformation of the group X to one of the other can be easily performed according to known techniques starting from the corresponding compound of formula (1). For example, the introduction of the double bond in position a or b, can be performed by reaction of dichlorodicyanoquinone (DDQ) with the corresponding silylenolethers or by oxidation with mercuric acetate of the saturated corresponding compound obtained as described above. The transformation of group X can be performed via the corresponding enoltriflates and their carbonylation in the presence of palladium diacetate, triphenylphosphine and the suitable nucleophilic reagent (alcohol, amine, nitro-group).

For this purpose, a number of products of formula (I) were tested as regards their capacity for modifying seed germination.

The introduction of compounds of formula (I) in various concentrations into the culture medium notably modified germination of Arabidopsis Thaliana Columbia (Col 0) seeds, kept in the dark for 10 days, as compared to the germination of non-treated seeds.

The effects observed on the treated seeds (i.e., lower growth of the hypocotyledons, development of cotyledons, and budding of the primary leaves) were similar to those described for seeds of plants genetically mutated as regards the DET2 enzyme, this indicating that the compounds of formula (I) are effective inhibitors in regard to this enzyme.

This observation indicates that the compounds of formula (I), in so far as they are inhibitors of the 5-alpha-reductases, and in particular of DET2 in plants, may be used to modify the germination of the seeds in the dark (if applied on the seeds) and modify the growth of the plants in the light (if applied on the plants). The possible industrial applications may thus regard the increase in germination of seeds of plants useful in agriculture and/or the reduction in the growth of harmful plants.

EXAMPLE

Batches of 25 seeds of Arabidopsis Thaliana Columbia (Col 0) were made to germinate in a suitable culture medium consisting of 0.5 ×MS at pH 5.7, containing 1% sucrose, 1×Vitamin B5 Gamborg, and 0.8% phyto-agar in the presence of the 1,2,5,6-tetrahydro-(11H)benzo[c]quinolizin-3-one inhibitor at the concentrations of 0, 0.01, 0.1, 1 and 10 micromolar. After two hours of treatment in light, the seeds were covered with three layers of aluminium foil and kept at 21° C. in a growth chamber. After 10 days in the dark, the length of the hypocotyledons was measured. In the plants not treated with the inhibitor, the length measured was approximately 15-16 mm, whereas in the treated plants the hypocotyledons were progressively shorter as the concentration of inhibitor used was increased.

A reduction of 50% in the hypocotyledons as compared to the controls was found for the seeds treated with a concentration of 0.1 micromolar of inhibitor. This indicates that the inhibitor at that concentration determines a control over germination of seeds in the dark.

What is claimed is:

1. A method for regulating plant growth, said method comprising: contacting a plant with an effective amount of at least one benzo(c)quinolizine compound or salt thereof of formula (I):

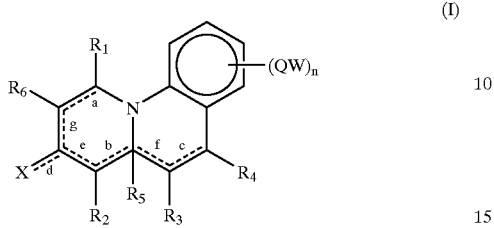

wherein:
$R_1$, $R_2$, $R_3$, $R_4$ and $R_6$ which are the same or different from one another, are chosen from the group consisting of H, $C_{1-8}$ alkyl, $C_{2-8}$ alkenyl, $C_{2-8}$ alkynyl, $C_{3-6}$ cycloalkyl, aryl, heterocycle, halogen, CN, azide, NRR', $C_{1-8}$ alkylamine, arylamine, $C_{1-8}$ alkyloxy, aryloxy, COOR, and CONRR', where R and R', which are the same or different from one another, are chosen from the group consisting of H, $C_{1-8}$ alkyl, aryl, heterocycle, aryl-$C_{1-8}$ alkyl, and cyclo-alkyl;

$R_5$ is chosen from the group consisting of H, $C_{1-8}$ alkyl, aryl-$C_{1-8}$ alkyl, COOR, CN, aryl, heterocycle, and the $C_{1-8}$ alkyl heterocycle;

X is chosen from the group consisting of O, C(=O)R, COOR, $NO_2$, and CONNR', in which R and R' are as defined above;

Q is chosen from the group consisting of single-bond, $C_{1-8}$ alkyl, $C_{2-8}$ alkenyl, $C_{2-8}$ alkynyl, cyclo-alkyl, CO, CONR, and NR, where R is as defined above;

W is chosen from the group consisting of H, $C_{1-8}$ alkyl, $C_{2-8}$ alkenyl, $C_{2-8}$ alkynyl, cycloalkyl, trifluoromethyl, $C_{1-8}$ alkoxy, $C_{1-8}$ alkoxy-$Cl_{1-8}$ alkyl, aryl-$C_{1-8}$alkyl, aryl, aryloxy, arylamine, $C_{1-8}$ alkylcarbonyl, arylcarbonyl, halogen, CN, NRR', $C_{1-8}$ alkylamine, and heterocycle:

n is 1, 2, 3, or 4;

the mark ------ indicates that the respective bonds a,b,c,d,e,f, and g are single or double bonds, considering that when b or f are a double bond, the $R_5$ group is absent.

2. A method for regulating plant growth as defined in claim 1 wherein a 5-alpha reductase steroidal enzyme DET2 in said plant is inhibited.

3. A method for regulating plant growth or modifying seed germination which comprises contacting said plants or seeds with an effective amount of a benzo(c)quinolizine compound of formula (I):

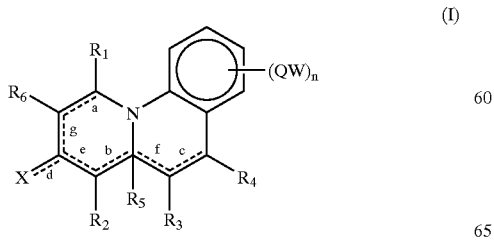

wherein:
$R_5$=H or heterocycle;
X=O;
Q=single-bond, CO, CONR, or NR W=H, F, Cl, Br, Me, tert-butyl, $C_{1-8}$ alkoxy, 2,5-dimethylhexyl, trifluoromethyl, 2,5-(di-trifluoromethyl)-phenyl, 4-methoxy-phenyl, 4-fluoro-phenyl, phenyl, phenyl-$C_{1-8}$ alkyl, $C_{1-8}$ alkylcarbonyl, or phenylcarbonyl;
n=1 or 2;
$R_1$, $R_2$, $R_3$, $R_4$ and $R_6$=H, Me, CN, phenyl, COOR, or CONRR' where R and R', which are the same or different from one another, are chosen from the group consisting of H, $C_{1-8}$ alkyl, aryl, heterocycle, and cyclo-alkyl.

4. A method for regulating plant or modifying seed germination:

1,2,4,4a,5,6 hexahydro-(11H)-benzo(c)quinolizin-3-one; 8-chloro-1,2,4,4a,5,6 hexahydro-(11H)-benzo(c)quinolizin-3-one;

1,2,4,4a,5,6 hexahydro-8-methyl-(11H)-benzo(c)quinolizin-3-one;

1,2,4,4a,5,6 hexahydro-4-methyl-(11H)-benzo(c)quinolizin-3-one;

1,2,4,4a,5,6 hexahydro-1-methyl-(11H)-benzo(c)quinolizin-3-one;

1,2,5,6-tetrahydro-(11H)-benzo(c)quinolizin-3-one;

8-chloro-1,2,5,6-tetrahydro-(11H)-benzo(c)quinolizin-3-one;

8-methyl-1,2,5,6-tetrahydro-(11H)-benzo(c)quinolizin-3-one;

4-methyl-1,2,5,6-tetrahydro-(11H)-benzo(c)quinolizin-3-one;

1-methyl-1,2,5,6-tetrahydro-(11H)-benzo(c)quinolizin-3-one;

4,4a,5,6-tetrahydro-(11H)-benzo(c)quinolizin-3-one;

5,6-dihydro-(11H)-benzo(c)quinolizin-3-one;

8-chloro-4,4a,5,6-tetrahydro-(11H)-benzo(c)quinolizin-3-one;

8-chloro-1 methyl-4,4a,5,6-tetrahydro-(11H)-benzo(c)quinolizin-3-one;

8-methyl-4,4a,5,6-tetrahydro-(11H)-benzo(c)quinolizin-3-one; (cis) and (trans) 4-methyl-4,4a,5,6-tetrahydro-(11H)-benzo(c)quinolizin-3-one;

8-chloro-4 methyl-1,2,5,6,-tetrahydro-(11H)-benzo(c)quinolizin-3-one;

4, 8-dimethyl-1,2,5,6,-tetrahydro-(11H)-benzo(c)quinolizin-3-one;

(cis) and (trans) 4,8-dimethyl-4,4a,5,6-tetrahydro-(11H)-benzo(c)quinolizin-3-one; and (cis) and (trans) 8-chloro-4-methyl-4,4a,5,6-tetrahydro-(11H)-benzo(c)quinolizin-3-one.

5. A compound of formula (I):

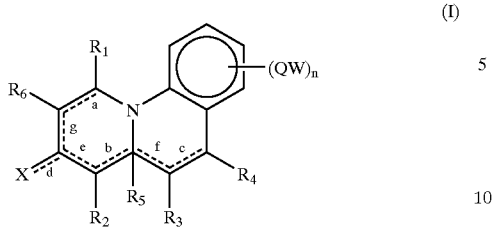

(I)

in which:
R1, R2, R3, R4 and R6, which are the same or different from one another, are chosen from the group consisting of H, $C_{1-8}$ alkyl, $C_{2-8}$ alkenyl, $C_{2-8}$ alkynyl, $C_{3-6}$ cycloalkyl, aryl, heterocycle, halogen, CN, azide, NRR', $C_{1-8}$ alkylamine, arylamine, $C_{1-8}$ alkyloxy, aryloxy, COOR, and CONRR', where R and R', which are the same or different from one another, are chosen from the group consisting of H, $C_{1-8}$ alkyl, aryl, heterocycle, aryl-$C_{1-8}$ alkyl, and cyclo-alkyl;

X is chosen from the group consisting of O, C(=O)R, COOR, $NO_2$, and CONNR', in which R and R' are as defined above;

Q is chosen from the group consisting of single-bond, $C_{1-8}$ alkyl, $C_{2-8}$ alkenyl, $C_{2-8}$ alkynyl, cyclo-alkyl, CO, CONR, and NR, where R is as defined above;

W is chosen from the group consisting of H, $C_{1-8}$ alkyl, $C_{2-8}$ alkenyl, $C_{2-8}$ alkynyl, cycloalkyl, trifluoromethyl, $C_{1-8}$ alkoxy, $C_{1-8}$ alkoxy-$C_{1-8}$ alkyl, aryl-$C_{1-8}$ alkyl, aryl, aryloxy, arylamine, $C_{1-8}$ alkyl-carbonyl, arylcarbonyl, halogen, CN, NRR', $C_{1-8}$ alkylamine, and heterocycle:

n is 1, 2, 3, or 4;

the mark ------ indicates that the respective bonds a,b,c,d,e,f, and g are single or double bonds, considering that when b or f are a double bond, the $R_5$ group is absent;

R5=$C_{1-8}$ alkyl-aryl or $C_{1-8}$ alkyl heterocycle, with the proviso that when $R_5$ is benzyl at least one of $R_1$, $R_6$, X and $R_2$ is not a COOR group.

6. A Benzo(c)quinolizine compound selected from the group consisting of:
   4a-benzyl-4,4a,5,6-tetrahydro-(11H)-benzo[c]quinolizin-3-one;
   8 chloro-4a-benzyl-4,4a,5,6-tetrahydro-(11H)-benzo[c]quinolizin-3-one.

7. A method for modifying plant seed germination, said method comprising: contacting seeds with an effective amount of at least one benzo (c) quinolizine compound or salt thereof of formula (I):

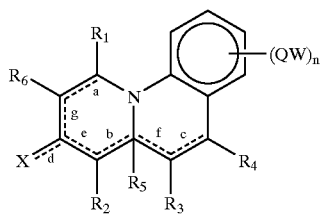

(I)

wherein:
$R_1$, $R_2$, $R_3$, $R_4$ and $R_6$, which are the same or different from one another, are chosen from the group consisting of H, $C_{1-8}$ alkyl, $C_{2-8}$ alkenyl, $C_{2-8}$ alkynyl, $C_{3-6}$ cycloalkyl, aryl, heterocycle, halogen, CN, azide, NRR', $C_{1-8}$ alkylamine, arylamine, $C_{1-8}$ alkyloxy, aryloxy, COOR, and CONRR', where R and R', which are the same or different from one another, are chosen from the group consisting of H, $C_{1-b\ 8}$ alkyl, aryl, heterocycle, aryl-$C_{1-8}$ alkyl, and cyclo-alkyl;

$R_5$ is chosen from the group consisting of H, $C_{1-8}$ alkyl, aryl-$C_{1-8}$ alkyl, COOR, CN, aryl, heterocycle, and the $C_{1-8}$ alkyl heterocycle;

X is chosen from the group consisting of O, C(=O)R, COOR, $NO_2$, and CONNR', in which R and R' are as defined above;

Q is chosen from the group consisting of single-bond, $C_{1-8}$ alkyl, $C_{2-8}$ alkenyl, $C_{2-8}$ alkynyl, cyclo-alkyl, CO, CONR, and NR, where R is as defined above;

W is chosen from the group consisting of H, $C_{1-8}$ alkyl, $C_{2-8}$ alkenyl, $C_{2-8}$ alkynyl, cycloalkyl, trifluoromethyl, $C_{1-8}$ alkoxy, $C_{1-8}$ alkoxy-$C_{1-8}$ alkyl, aryl-$C_{1-8}$ alkyl, aryl, aryloxy, arylamine, $C_{1-8}$ alkyl-carbonyl, arylcarbonyl, halogen, CN, NRR', $C_{1-8}$ alkylamine, and heterocycle:

n is 1, 2, 3, or 4;

the mark ------ indicates that the respective bonds a,b,c,d,e,f, and g are single or double bonds, considering that when b or f are a double bond, the $R_5$ group is absent.

8. A method as set forth in claim 7, wherein the effective amount of said benzo(c)quinolizine compound ranges from 0.01 to 10 micromoles.

9. A method as set forth in claim 7, wherein said plant seeds are treated with said benzo(c)quinolizine compound in the light for approximately 2 hours.

10. A method as set forth in claim 7, wherein said plant seeds are incubated in the dark for approximately 10 days.

11. The method as set forth in claim 7, wherein the plant seeds are Arabidopsis.

12. A method as defined in claim 7 wherein a 5-alpha reductase steroidal enzyme DET2 in said seed is inhibited.

* * * * *